United States Patent [19]

Cordes et al.

[11] 4,156,736

[45] May 29, 1979

[54] SUPERSATURATED ISOSORBIDE DINITRATE SOLUTION, PROCESS FOR ITS PRODUCTION AND ITS USE

[75] Inventors: Günter Cordes; Ulrich Münch, both of Leichlingen; Ewald Giesselmann, Monheim, all of Fed. Rep. of Germany

[73] Assignee: Sanol Schwarz-Monheim GmbH, Monheim, Fed. Rep. of Germany

[21] Appl. No.: 798,639

[22] Filed: May 19, 1977

[30] Foreign Application Priority Data

May 28, 1976 [DE] Fed. Rep. of Germany ....... 2623800
Dec. 29, 1976 [DE] Fed. Rep. of Germany ....... 2659393

[51] Int. Cl.$^2$ ............................................. A61K 31/34
[52] U.S. Cl. .................................................... 424/285
[58] Field of Search ............................... 424/285, 180

[56] References Cited

U.S. PATENT DOCUMENTS

| | | | |
|---|---|---|---|
| 3,911,137 | 10/1975 | Miki et al. ............................ | 424/319 |
| 3,972,995 | 8/1976 | Tsuk et al. .............................. | 424/28 |

Primary Examiner—Stanley J. Friedman
Attorney, Agent, or Firm—Hammond & Littell

[57] ABSTRACT

Supersaturated aqueous to organic solvent solution of isosorbide dinitrate, process of preparation at elevated temperatures, and use of the supersaturated solutions for the production of infusion solutions.

13 Claims, No Drawings

SUPERSATURATED ISOSORBIDE DINITRATE SOLUTION, PROCESS FOR ITS PRODUCTION AND ITS USE

BACKGROUND OF THE INVENTION

Isosorbide dinitrate (ISD) has been given orally like other nitric acid esters for angina pectoris in the form of tablets or capsules with good results for a long time. Recently it has been shown that apart from this traditional indication ISD can also be used for the following diseases: for heart insufficiency of the left ventricle, for recent myocardinfarct as well as for incipient edema of the lungs.

For the preceding indications the parenteral application offers advantages compared with the oral application since

- the patients with the aforementioned diseases are in hospitals;
- a correct, controlled dosage by infusion is necessary; and
- when parenterally applied the metabolism of the active substance during the first passage through the liver is avoided, which leads, as is well known, to a decomposition of essential amounts of active substance to mononitrates and isosorbide when orally applied.

When ISD is parenterally applied, dosage should be made up individually according to the acuteness of the respective case. The ISD concentration in ampules for the production of infusion solutions aimed at by doctors should be 1 mg/ml (= g/l), 2 mg/ml (= 2 g/l) or more, since in this manner.

- even the lowest possible starting concentration at the beginning of a treatment could be adjusted in the infusion solution;
- a sufficiently high concentration for the treatment could be attained without applying very large liquid amounts; and
- the calculation of concentrations would be considerably simplified by a simple ratio of numbers (e.g., 1 mg ISD/ml).

In general, the lowest concentration with which therapy can be started is regarded as 5 mg ISD/250 ml infusion solution. If ampules with ISD solutions having a concentration of 1 mg/ml were available, 5 ml of these ISD solutions would have to be diluted to 250 ml infusion solution. Then the dosage could be increased so that 10 mg ISD or even more a day could be applied to the patients.

On the basis of experiments preceding the invention (examples 1 to 2) the production of an aqueous ISD solution having a concentration of 1 mg/ml seemed to be impossible. At room temperature a saturation value of about 0.7 g ISD/l was found. These experiments were carried out in the presence of solid ISD in a manner which is usual to find out saturation values; ISD was dissolved in water up to saturation at room temperature or it crystallized from an supersaturated solution which had been cooled to room temperature. The results correspond to published data. From the following table 1 there follows that the older published data (caused by inexactness) vary within a broad range and in the meantime this range has been limited to limits of about 0.5 and 0.7 g/l so that this range has been corrected.

Table 1

| solubility of ISD in water (g/l) | Year | Quotation |
|---|---|---|
| 2 | 1959 | Med. Prom. SSSR 13 (1959) 18 – 20 according to CA 54 (1960) Quotation 8647 h |
| 1.1 | 1968 | Merck Index (1968) 593 |
| 0.001089 | 1968 | Merck Index (1968) 593 |
| <0.5 | 1975 | Anal. Profiles Drug Subst. 4 (1975) 231 |
| 0.68 | 1975 | Needleman, Organic Nitrates, Springer (1975) 17 |

OBJECTS OF THE INVENTION

An object of the present invention is to obtain a supersaturated aqueous isosorbide dinitrate solution having a content of isosorbide dinitrate in the range of more than the saturation value at room temperature temperature up to 2.5 g/l.

This and other objects of the invention will become more apparent as the description thereof proceeds.

DESCRIPTION OF THE INVENTION

However, the inventors have surprisingly found out that it is possible to produce ISD solutions having concentrations beyond the saturation value at room temperature when the production is carried out in the absence of solid ISD. It is surprising and useful that such supersaturated aqueous ISD solutions can also be used for therapeutical purposes since they are stable in an unforeseeable manner so that they can be stored without any changes for long periods (at least for months). This is especially surprising since it was not possible to fill supersaturated solutions into containers, e.g., ampules, without any crystallization on a technical scale unless the solutions, the ampules and the whole filling equipment were maintained at an elevated temperature. The use of supersaturated aqueous ISD solutions for the production of, e.g., infusion solutions is absolutely simple since in such cases the said supersaturated ISD solutions are diluted.

One embodiment of the invention concerns an supersaturated aqueous ISD solution.

This solution may contain ISD in the range of beyond the saturation value at room temperature up to 2.5 g/l, e.g., 1.0 or 2.0 g/l.

According to the invention the supersaturated aqueous ISD solution may in addition contain substances, e.g., sodium chloride, which are usual for isotonic solutions.

When according to the invention an supersaturated aqueous ISD solution is produced, ISD is completely and according to a concentration beyond the saturation value at room temperature dissolved in an aqueous medium at a raised temperature, the solution is filled into containers (if desired after filtration) at a raised temperature, the containers are closed and then cooled. Preferably ampules are used as the said containers.

It is possible to carry out the process at a raised temperature of at least 50 degrees centigrade, e.g., of at least 80 degrees centigrade.

It is possible to produce a solution having an ISD concentration of 1 g/l at at least 80 degrees centigrade; then the process including the filling is carried out at at least 50 degrees centigrade.

It is possible to combine ISD with water in a ratio of 1:1,000 and to increase the temperature to at least 80 degrees centigrade while stirring. When a clear solution has resulted, the said solution is maintained at a temperature of at least 50 degrees centigrade, filtrated through a suitable filter, if desired, and filled into ampules with any content. Then it is possible to sterilize the ampules in the usual manner in superheated steam according to the methods of the Deutsches Arzneibuch.

When the solution has been filled into the said containers and ampules, respectively, and sealed it is possible to heat the solution for, e.g., 15 minutes to at least 95 degrees centigrade, preferably 121 degrees centigrade.

However, in the event of particular diseases, it is necessary to give the patients even larger amounts of ISD by infusion than it is possible with supersaturated ISD solutions based on water as a single solvent.

According to another embodiment of the invention this problem is solved by an supersaturated aqueous ISD solution which contains a physiologically acceptable organic solvent (which is preferably suitable for infusions), e.g. alcohols, preferably polyhydric aliphatic alcohols, more preferably $C_{3-4}$-diols.

The solution according to the invention may contain 0.5 or more, preferably 5, 10, 20 or 50 or more, and more preferably 100% organic solvent based on the total amount of organic solvent and water.

The organic solvent is 1.2-proxyleneglycol, for example, which is preferably present in an amount of 100% based on the total amount of organic solvent and water. The ISD content may be in the range of beyond the saturation value at room temperature up to 30 g/l, e.g., up to 20 g/l.

For the production of ISD solution according to the invention ISD is completely and according to a concentration beyond the saturation value at room temperature dissolved at a raised temperature in a liquid medium which contains water and up to 100% of a physiologically acceptable organic solvent based on the total amount of organic solvent and water, the solution is (if desired after filtration) filled into containers at a raised temperature, the containers are closed and then cooled. It is possible to dissolve ISD at an elevated temperature of at least 50 degrees centigrade, e.g., about 80 degrees centigrade or more and to carry out the other steps including the filling at a temperature of at least 30 degrees centigrade, e.g. about 40 degrees centigrade or more.

Preferably the containers containing the solution are heated for at least 15 minutes to at least 95 degrees centigrade, preferably about 121 degrees centigrade.

It is possible to use 1,2-propyleneglycol as an example of a liquid medium. Further, it is possible to produce at about 80 degrees centigrade or more a solution having an ISD concentration of e.g. 20 g/l; then the process including the filling may be carried out at e.g. at least 30 degrees centigrade, e.g. about 40 degrees centigrade or more.

According to the invention special care is taken that the ISD solution doesn't become cold during the complete process of production, filtration and filling, which is different from the usual practice for the production of solutions which are filled into containers, e.g. ampules. The equipment used for production and filling is therefore best provided with special tempering means.

Ampules are suitable containers; they may be sterilized according to the methods of Deutsches Arzneibuch.

ISD solutions according to the invention may be used for the production of infusion solutions.

In the following the invention is described by examples in more detail.

EXAMPLE 1

Finely powdered ISD was shaken together with water at 24 degrees centigrade in a glass bottle with an automatic shaking apparatus for several hours. The ISD amount fed was so great that even after shaking a considerable excess of undissolved ISD remained. Then the undissolved ISD was filtrated off; the ISD content of the clear solution was examined by means of the phenol/disulfonic acid method. The evaluation was made by comparison with a standard solution which contained pure ISD. An ISD saturation concentration of 0.6858 mg/1.0 ml solution was found.

Details of the Experiment

Standard weight 39.94 mg/50 ml (Acetone/water mixture);

For the examination 0.5 ml of this standard solution were used;

Extinction of the standard solution = 0.396;

0.5 ml of the solution to be examined for comparison;

Extinction of the solution to be examined = 0.340.

EXAMPLE 2

Finely powdered ISD was stirred with a magnetic stirrer at 50 degrees centigrade in water for one hour. Then the solution was left at room temperature for 24 hours and undissolved ISD was filtrated off. An ISD saturation concentration of 0.76 mg/ml was found in the filtrate.

Details of the Experiment

Standard weight 39.65 mg/50 ml (Acetone/water mixture);

Extinction of the standard solution = 0.416;

Extinction of the solution to be examined 32 0.396.

EXAMPLE 3

1000 ml distilled water were added to 1 g ISD and 9 g sodium chloride with stirring. The mixture was heated to about 50 degrees centigrade until a clear solution resulted. The solution was filtrated and filled into ampules. The ampules were closed and sterilized in superheated steam at 121 degrees centigrade for about 15 minutes.

After the production the ISD content of some samples of these ampules was examined. Some other samples were stored in a refrigerator at 10 degrees centigrade and in a deep freezer, respectively, at minus 20 degrees centigrade for some time and then analyzed. Finally a sample was stored at room temperature for a long time; then its ISD content was examined. No samples showed crystals.

A quantative thin layer chromatography analyzing method was developed to examine the ISD. This method guaranteed that only undecomposed ISD was taken into consideration since possible decomposition products were separated from the pure ISD by chromatography. With this specific analyzing method it was possible to find out whether changes had appeared during the production or the storage. The results of the examinations are listed in the following table 2.

Table 2

| Experiment | Date of Production | Storage Temperature | Storage Time | ISD content (mg/ml) | Analyzing method |
|---|---|---|---|---|---|
| 132 a | 7/73 | RT | 0 | 1.045 | direct DC |
| 327 b | 4/74 | RT | a few days | 1.032 | polarogr. |
|  |  |  |  | 1.065 | " |
|  |  |  |  | 1.040 | " |
| 327 b | 4/74 | RT | 15 months | 1.007 | direct DC |
| 626 | 4/75 | RT | a few days | 0.970 | direct DC |
|  |  |  |  | 0.991 | " |
|  |  |  |  | 0.977 | " |
| 626 | 4/75 | RT & −20° C. | 3 months 1 day | 0.98 | direct DC |
| C-1 | 7/75 | RT | 1–2 days | 0.996 | direct DC |
| C-2 | 7/75 | RT | " | 1.026 | " |
| C-4 | 7/75 | RT | " | 1.016 | " |
| 726 | 7/75 | RT | 2 days | 1.099 | direct DC |
| 726 | 7/75 | +7° C. | 2 days | 1.057 | direct DC |

Remarks: RT = room temperature
DC = thin layer chromatography

EXAMPLE 4

ISD solutions having a concentration of about 2.5 mg ISD/ml were produced at a temperature of 80° C., filled into ampules and sterilized for 15 minutes at 121° C. These solutions which had been filled into ampules showed even after long storage no changes as can be seen from the following table 3.

Table 3

| Experiment | Date of Production | Storage Temperature | Storage Time | ISD content (mg/ml) | Analyzing method |
|---|---|---|---|---|---|
| C-5 | 10/75 | RT | 1 day | 2.48 | direct DC |
| C-5 | 10/75 | +7° C. & RT | 1 month 6 months | 2.53 2.51 | colorimetrically direct DC |
| 965 | 5/76 | RT | 1 day | 2.58 2.65 | colorimetrically direct DC |

EXAMPLE 5 AND COMPARATIVE EXAMPLE 1

ISD was dissolved in 1,2-propylene glycol at a temperature of 80° C. up to a concentration of about 20 mg ISD/ml. The solution was filled into ampules (5 ml) which were closed. Some ampules were sterilized in superheated steam for 20 minutes at 121 degrees centigrade (example 5). The remaining ampules were not sterilized (comparative example 1).

About 10 days later both groups were examined. In each ampule of the comparative example ISD crystals had been formed. These ampules contained 23.06 mg ISD/ml. On the other hand no crystals were found in the ampules of example 5. These ampules contained 23.32 mg ISD/ml.

Then all ampules were stored in a refrigerator at 6 degrees centigrade; the ISD content was examined 6 and 12 days later. Again, in example 5 no crystals and no changein the previously found concentration were observed. On the other hand, in comparative example 1 the proportion of the crystals had increased; the ISD concentration was 13.63 mg ISD/ml after 6 days and 8.70 mg ISD/ml after twelve days.

We claim:

1. A process for the production of a supersaturated aqueous isosorbide dinitrate solution having a content of isosorbide dinitrate of beyond the saturation value at 24° C. to 2.5 g/l which consists essentially of completely dissolving an amount of isosorbide dinitrate in excess of the saturation value at 24° C. up to 2.5 g/l in an aqueous medium at a temperature of at least 50° C. up to a point wherein the desired supersaturation occurs, and cooling in the absence of solid isosorbide dinitrate.

2. The process of claim 1 wherein said dissolving step is conducted at at least 80° C. up to a point wherein the desired supersaturation occurs.

3. The process of claim 2 wherein said solution of isosorbide dinitrate is filled into its ultimate container in unitary dosage amounts before said cooling step.

4. The process of claim 3 wherein said container containing said unitary dosage amount is steam sterilized.

5. The process of claim 2 wherein said aqueous medium is water.

6. The process of claim 2 wherein said aqueous medium is an isotonic solution.

7. The supersaturated aqueous isosorbide dinitrate solution having a content of isosorbide dinitrate in the range of beyond the saturation value at 24° C. to 2.5 g/l produced by the process of claim 1.

8. The supersaturated aqueous isosorbide dinitrate solution having a content of from 1.0 g/l to 2.5 g/l produced by the process of claim 1.

9. The process for the production of a supersaturated isosorbide dinitrate solution having a content of isosorbide dinitrate of beyond the saturation value at 24° C. to 30 g/l and filled in containers for the production of infusion solutions which consists essentially of completely dissolving an amount of isosorbide dinitrate in excess of the saturation value at 24° C. up to 30 g/l, in a liquid medium containing from 0 to 100% of a physiologically-acceptable polyhydric aliphatic alcohol, with the remainder to 100%, of said liquid medium, water, at a temperature of at least 50° C. up to the point wherein the desired supersaturation occurs, filling said solution at said temperature into its ultimate container, in a unitary dosage amount, and cooling in the absence of solid isosorbide dinitrate.

10. The process of claim 9 wherein said container containing said unitary dosage amount is steam sterilized.

11. The process of claim 9 wherein said polyhydric aliphatic alcohol is 1,2-propylene-glycol.

12. The process of claim 9 wherein said dissolving step is conducted at at least 80° C. up to the point wherein the desired supersaturation occurs.

13. The supersaturated isosorbide dinitrate solution having a content of isosorbide dinitrate of beyond the saturation value at 24° C. to 30 g/l and filled into containers for the production of infusion solutions produced by the process of claim 9.

* * * * *

UNITED STATES PATENT AND TRADEMARK OFFICE
CERTIFICATE OF CORRECTION

PATENT NO.  : 4,156,736                          Page 1 of 2

DATED       : May 29, 1979

INVENTOR(S) : Gunter Cordes, Ulrich Munch and Edwald Giesselmann

It is certified that error appears in the above-identified patent and that said Letters Patent are hereby corrected as shown below:

| Col. | Line | |
|---|---|---|
| 1 | 34 | "(= g/l)" should be --(= 1 g/l)-- |
| 3 | 25 | "1.2" should be --1,2-- |
| 4 | 40 | "320.396" should be --0.396-- |
| 5 | Table 3 | line 4 "965" should be --966-- |
| 5 | 60 | "changein" should be --change in-- |
| 6 | 34 | "The" should be "A" |

UNITED STATES PATENT AND TRADEMARK OFFICE
CERTIFICATE OF CORRECTION

PATENT NO. : 4,156,736                    Page 2 of 2
DATED      : May 29, 1979
INVENTOR(S): Gunter Cordes, Ulrich Munch and Ewald Giesselmann It is certified that error appears in the above–identified patent and that said Letters Patent are hereby corrected as shown below:

| Col. | Line | |
|---|---|---|
| 6 | 11 | delete [desired supersaturation occurs] and insert --selected amount of isosorbide dinitrate is completely dissolved-- |
| 6 | 45 | same as above |
| 3 | 15 | "an supersaturated" should be --a supersaturated-- |

Signed and Sealed this

Twentieth Day of May 1980

[SEAL]

Attest:

SIDNEY A. DIAMOND

Attesting Officer

Commissioner of Patents and Trademarks